United States Patent
Rappel et al.

(10) Patent No.: US 10,964,232 B2
(45) Date of Patent: Mar. 30, 2021

(54) APPARATUS, METHOD AND SYSTEM FOR MICROSURGICAL SUTURE TRAINING

(71) Applicants: James Kolenchery Rappel, Singapore (SG); Amitabha Lahiri, Singapore (SG)

(72) Inventors: James Kolenchery Rappel, Singapore (SG); Amitabha Lahiri, Singapore (SG)

(73) Assignee: Digital Surgicals PTE. LTD., Singapore (SG)

( * ) Notice: Subject to any disclaimer, the term of this patent is extended or adjusted under 35 U.S.C. 154(b) by 1332 days.

(21) Appl. No.: 14/665,054

(22) Filed: Mar. 23, 2015

(65) Prior Publication Data

US 2015/0194075 A1   Jul. 9, 2015

Related U.S. Application Data

(62) Division of application No. 13/667,066, filed on Nov. 2, 2012, now Pat. No. 9,070,306.

(51) Int. Cl.
| | |
|---|---|
| *G09B 23/30* | (2006.01) |
| *G09B 23/28* | (2006.01) |
| *G16H 20/40* | (2018.01) |

(52) U.S. Cl.
CPC ............. *G09B 23/30* (2013.01); *G09B 23/28* (2013.01); *G16H 20/40* (2018.01)

(58) Field of Classification Search
CPC ................................ G09B 23/28; G09B 23/30
(Continued)

(56) References Cited

U.S. PATENT DOCUMENTS

| | | | | |
|---|---|---|---|---|
| 6,002,136 A | * | 12/1999 | Naeem | ................... B82Y 35/00 |
| | | | | 250/442.11 |
| 8,656,536 B1 | * | 2/2014 | Sorg | ................... A61G 13/1205 |
| | | | | 378/209 |

(Continued)

OTHER PUBLICATIONS

"Proceedings of the 2nd Biennial IEE/RAS-EMBS International Conference on Biomedical Robotics and Biomechatronics," Solis et al., Scottsdale, AZ, Oct. 19-22, 2008.*
(Continued)

*Primary Examiner* — James B Hull
*Assistant Examiner* — Jennifer L Korb
(74) *Attorney, Agent, or Firm* — Clements Bernard Walker; Lawrence A. Baratta, Jr.; Jacob P. Beers

(57) ABSTRACT

Systems and methods of microsuture training include receiving an image or video of a suture; extracting features of the suture from the image or video; scoring the suture based on the extracted features and based on a rating and complexity of the suture to determine a quality of the suture in an objective manner. A suture training system includes a suture training apparatus configurable with a plurality of orientations of simulated or actual tissue to simulate natural anatomical orientations encountered in actual surgery, wherein the plurality of simulated tissue orientations are objective based on fiducial markings on the suture training apparatus; and an image analysis system configured to receive an image or video of a suture performed on the suture training apparatus; extract features of the suture from the image or video; score the suture.

20 Claims, 17 Drawing Sheets

(58) Field of Classification Search
USPC .................................... 434/262, 267
See application file for complete search history.

(56) References Cited

U.S. PATENT DOCUMENTS

| | | | |
|---|---|---|---|
| 2008/0118902 A1* | 5/2008 | Matsumura | G09B 23/30 |
| | | | 434/272 |
| 2012/0189996 A1* | 7/2012 | Hager | G09B 7/00 |
| | | | 434/262 |
| 2013/0238021 A1* | 9/2013 | Gross | A61B 17/06166 |
| | | | 606/228 |
| 2015/0086955 A1* | 3/2015 | Poniatowski | G09B 23/28 |
| | | | 434/267 |

OTHER PUBLICATIONS

"50 Years of Image Analysis: Quantitative Microscopy from Television-Based Image Analyzer to Integrated Digital Software solutions," Pingel et al., https://www.leica-microsystems.com/science-lab/50-years-of-image-analysis/, Nov. 19, 2012.*

* cited by examiner

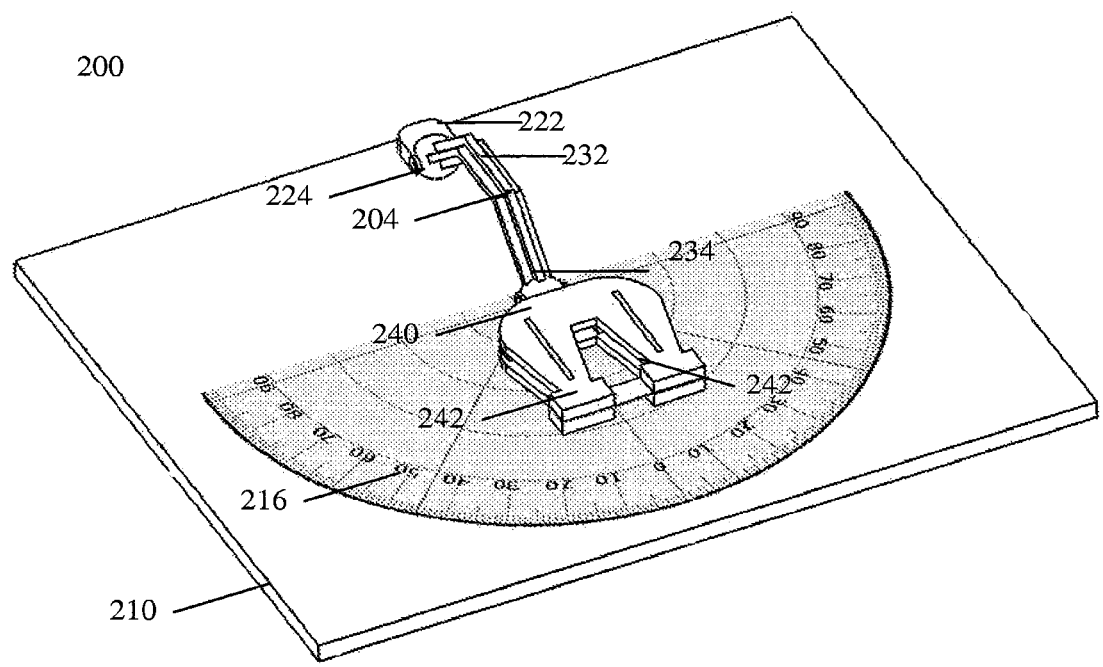
Fig 2.a
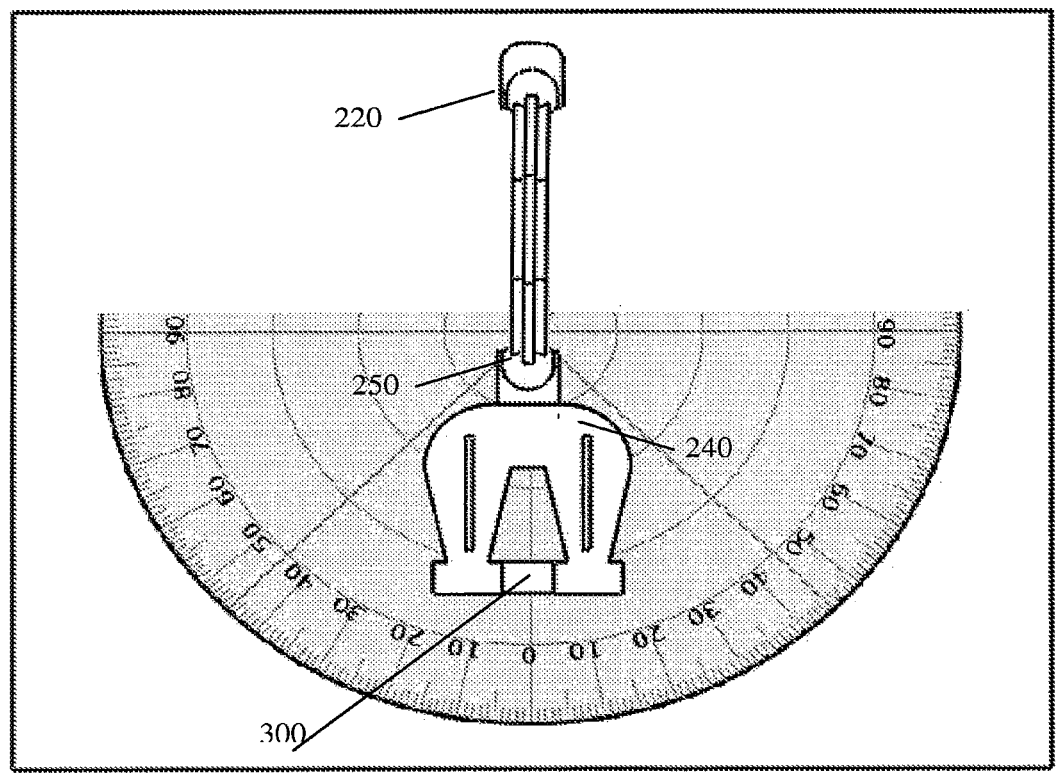
Fig 2.b

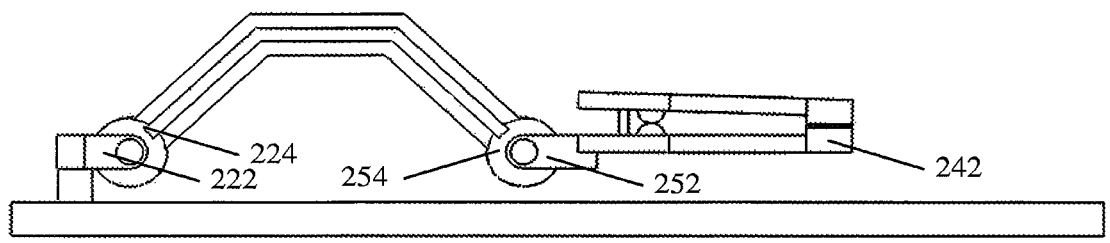
Fig 2.c
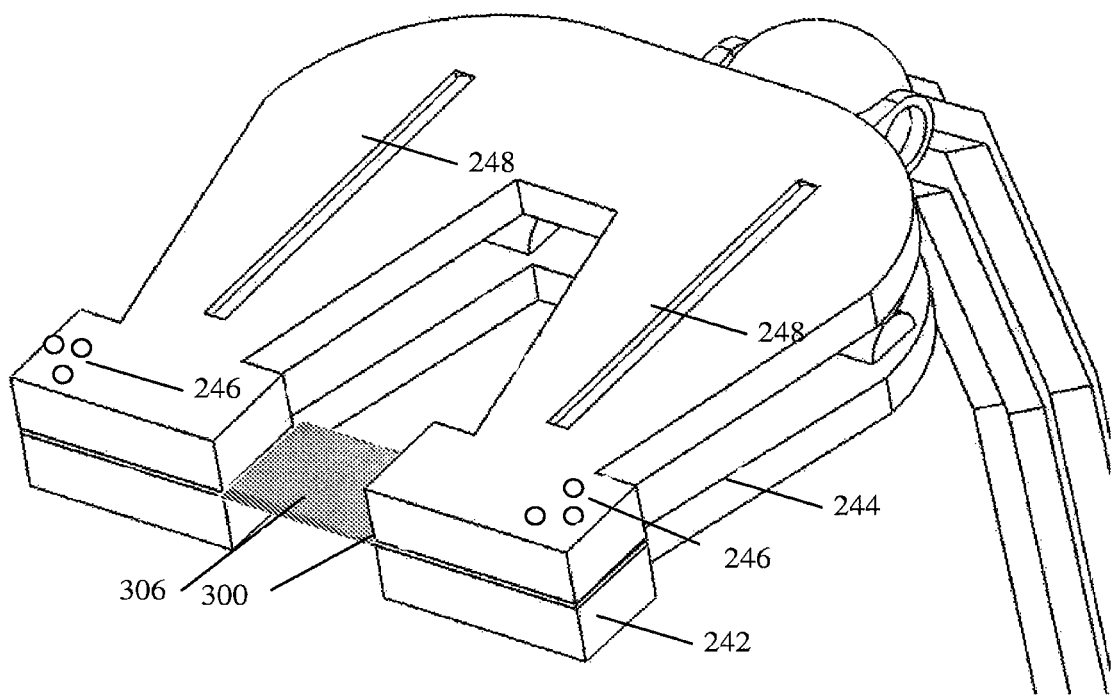
Fig 2.d

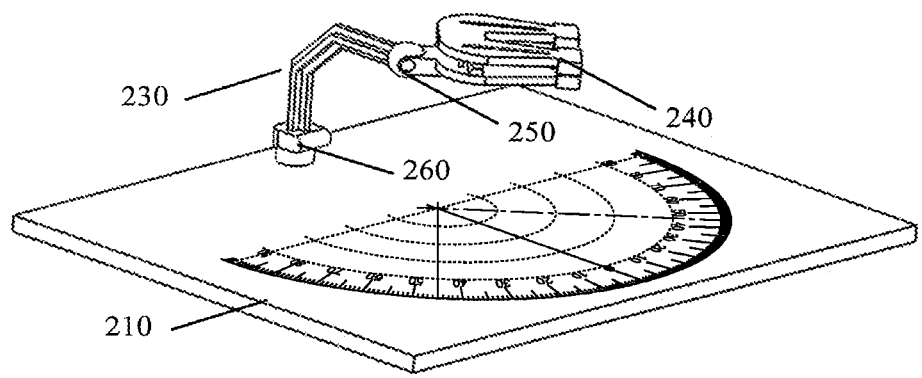
Fig 3.a
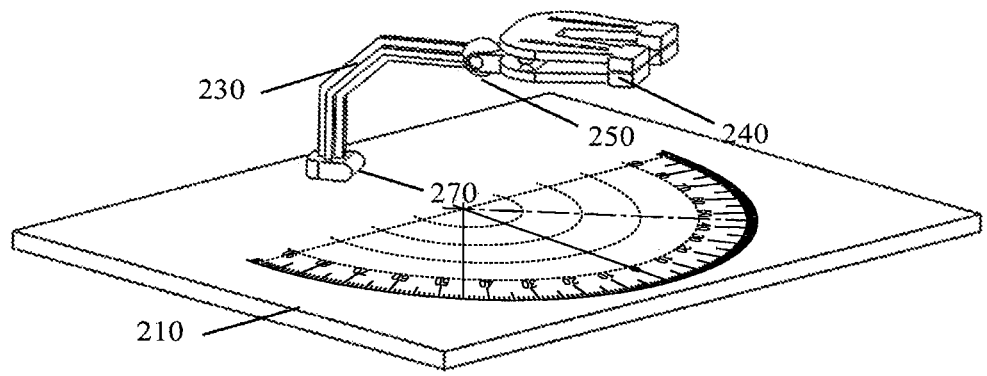
Fig 3.b

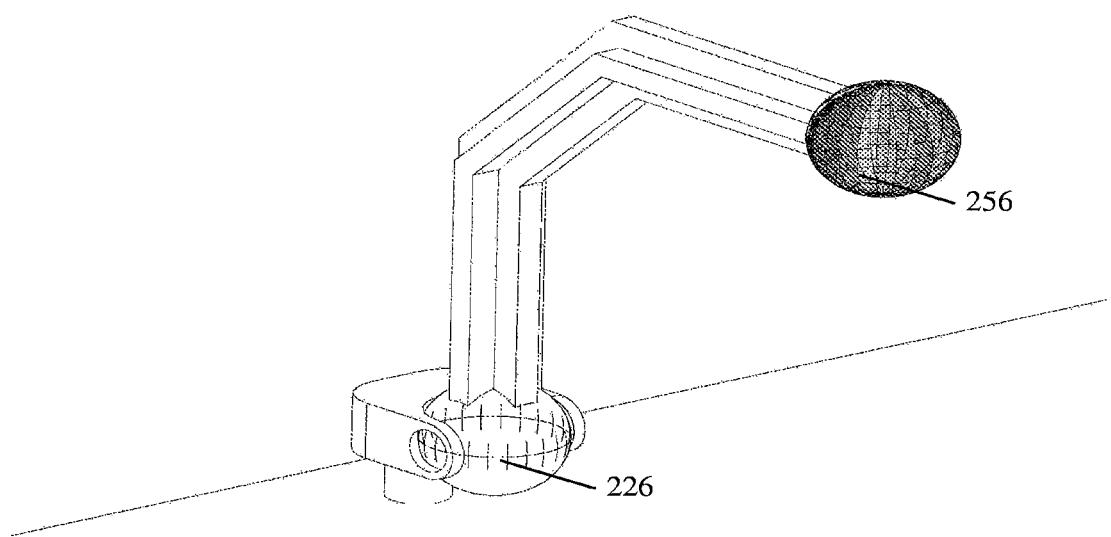
Fig. 3.c

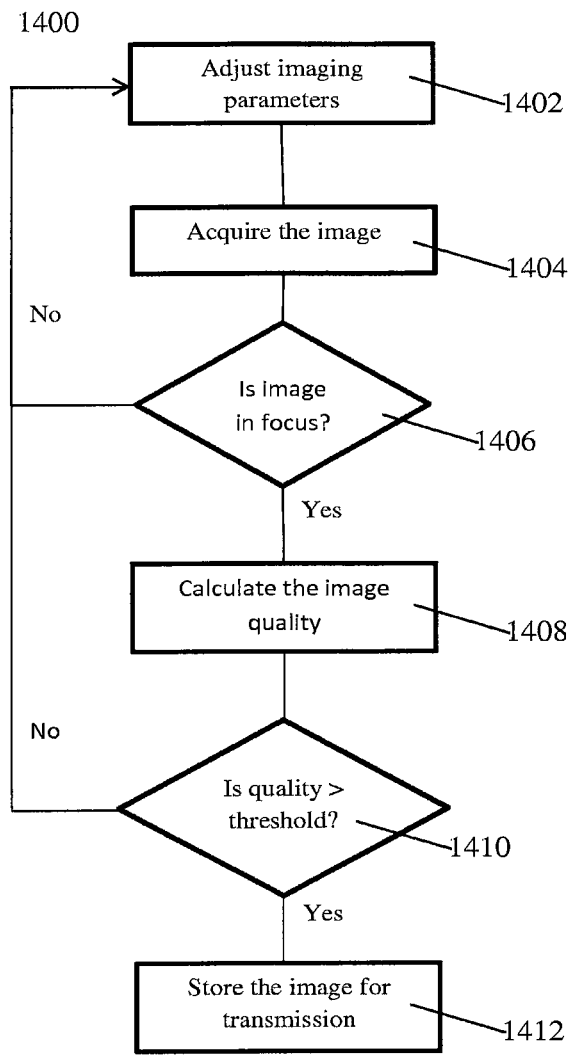
Fig. 18
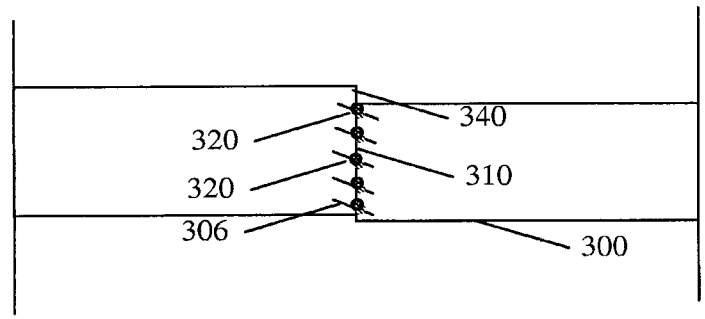
Fig.19 Suture on synthetic tissue

APPARATUS, METHOD AND SYSTEM FOR MICROSURGICAL SUTURE TRAINING

CROSS-REFERENCE TO RELATED APPLICATIONS

The present application/patent is a divisional of U.S. patent application Ser. No. 13/667,066, filed Nov. 2, 2012, and entitled "Apparatus, Method and System for Microsurgical Suture Training," the contents of which are incorporated by reference herein.

FIELD OF THE DISCLOSURE

The invention relates to an apparatus for microsurgical suture training, a method of processing a microsuture training image, and a microsuture training.

BACKGROUND OF THE DISCLOSURE

There is a set of basic surgical moves, which, when sequenced forms a surgical procedure. A fundamental difference between surgical procedures is the orientation of the surgical target upon which basic surgical moves are performed. For example, anastomosis is a key surgical procedure used in establishing continuity in the blood vessels. It consists of a series of steps to suture a vessel or a nerve, starting from grasping the tool, entering the tissue, exiting and tying the knot. However, depending on the orientation of the vessel, the basic movements become more complex. The practice of the surgical tasks such as tool grasping and suture placement is important so is practicing them in different anatomical orientations encountered in surgery. The practice of these surgical moves in natural anatomical positions improves surgery training.

Medical, dental and veterinary students, as well as more experienced doctors, dentists and veterinarians, learning new surgical techniques, must undergo extensive training before they are optimally qualified to perform surgery. It would be advantageous for students and medical personnel to obtain as much hands-on experience as possible, operating on actual or simulated body structures when learning surgical procedures. These skills are generally learned by observation and didactic instruction from an accomplished surgeon tutor. Learning of these basic skills can be enhanced by viewing video presentations of procedure-specific instructions. Such practice can shorten the learning curve in the operating room.

For example, a student may perform procedures on human cadavers or animals. Both are expensive. In addition, unnecessary surgery on animals is resisted for ethical and legal reasons. Moreover, objective assessment of surgical skill is difficult on animals or cadaver. A surgeon may be trained to a new surgical procedure, but the amount of training time is very insufficient to perfect the practice. Moreover, the training needs to be continuous to sustain the skill. Therefore, even practicing surgeons need a tool to train them outside the operating room. It is observed that an experienced surgeon makes, the less amount of and less number of movements to complete a surgical procedure, resulting less trauma of the surrounding tissue and improved healing time.

Presently, there exists virtual and non-virtual simulators on which to practice surgical skills. Most virtual simulators rely on sophisticated haptic sensors and software integrated with large computer systems that are immobile and often extremely expensive. Teaching institutions that can afford them are usually only able to purchase a limited quantity. Therefore, students often have restricted access and limited times to practice surgical techniques using virtual simulators. In addition, virtual simulators are used for more specialized and complex surgery techniques. For example, endoscopic vessel harvesting systems which are made to model a specific procedure are available. In these specialized prior-art systems, a specific procedure, for example, harvesting of the saphenous vein is modelled. Hence it cannot be adapted to practice newer surgery techniques since it does not teach the basic surgical skills. Basic surgical skills include cutting, knot-tying techniques, suturing techniques, dissection, clamping, clipping, grasping, ligating, cannulation, stapling, cauterization, and suture cutting, among others.

Repetitive practice of these skills is necessary to achieve competency and subsequent mastery characterized by rapidity, automaticity, and delicacy. Coordinated motions of both hands to move and stabilize tissues with the non-dominant hand and precise cutting, clamping, or suturing by the dominant hand are characteristic of most basic surgical tasks. A surgical simulation system ideally should provide facility to practice these basic skills.

Though there are some training tools and kits available, the effectiveness of such training tools are limited due to the disparity between the actual surgery and the surgery training. For example, Lumely's practice block allows synthetic vessels to be placed, divided and sutured for practice. The practice is limited to a 2D orientation and hence is of limited use. In real life surgery, the anatomical orientations are more complex and there is no method for objective analysis of the quality of the suturing.

Many other existing practice systems focus on providing real life simulations such as blood flow, but do not focus on improving surgeon's skills to manipulate the tools under anatomical orientations that restrict surgeon's movement. Many of the available systems present the simulated tissue in the horizontal plane, such as natural or synthetic specimens prepared and presented in a convenient horizontal plane. For example, latex sheets provided by 'Braun' allow simulation of suturing in various angles, but are limited to the horizontal plane.

A similar device called the anastomosis simulator is marketed by Sharpoint, which uses silicone tubes that simulate vessel anastomosis. It is also limited to simulation in one horizontal plane.

Existing systems ignore the fact that coordinated hand movements are difficult when surgical tissues are oriented in oblique or vertical plane, which is a more natural presentation of the clinical task. Hence, existing surgery training systems do not pose similar type of dexterity challenges as in a real surgery.

BRIEF SUMMARY OF THE DISCLOSURE

Existing surgery training systems are limited to training the surgeons in a convenient horizontal plane. They do not pose dexterity challenges of a real surgery where the tools have to be operated on vessels oriented in oblique or vertical plane. Hence a microsurgery training tool that offers similar dexterity challenges of actual surgery may be desirable for sharpening surgical skills.

Given the finer nature of the suture in microsurgery, identifying the good suture from bad suture can be difficult and time consuming. The identification of good suture from bad suture is important to depict the skill profile over time of practice. There are a number of types of errors that a trained surgeon may make. Identifying them may assist in fixing the errors and advising the right technique.

It is challenging in grading the surgery skills in-relation to a group of surgeons practicing in the same or similar facilities. Given enough training, each surgeon of the group must practice at the same level. Ranking can be used by surgeons to achieve better surgical skill in comparison to their peers. For a comparison to be possible, all surgeons in the population must be facing standardized dexterity challenges.

Given the finer nature of the suture in microsurgery, identifying a good suture from bad suture can be difficult and time consuming. The evaluation of the quality of suturing is manual and subjective. The success of the surgery depends on the suturing skills of the surgeon in closing the wound to prevent infection and creating appropriate strength on the tissues to enhance healing. A good suture leaves less scarring, and good sutures produce eversion of the tissue. There is a need for objective and standardized evaluation of the quality of the suture.

The silicone tubes used in existing systems do not allow for easy assessment of individual stitch or the spacing between the sutures. Both stitch and stitch spacing are parameters of assessing the accuracy of stitch placement and expertise in suturing.

In general terms in one aspect the present invention proposes a suture training apparatus configurable with a plurality of simulated tissue orientations to simulate natural anatomical orientations encountered in the actual surgery. This may be provided with two joint connections to allow 6 degrees of freedom. The apparatus allows manual orientation of the simulated tissue allowing the surgeon to acquire necessary skills for placing sutures in various planes of orientation.

It utilizes the observation that the human vascular system presents various three dimensional orientations for the vessels and consequently a number of three dimensional orientations for the surgeons to adapt the suturing technique to operate on the vessels. For example, end-to-end anastomosis requires orienting the tools orthogonal to the direction of the vessels, whereas end-to-side anastomosis requires orienting the tools in an oblique orientation to the vessels. By using the apparatus, the surgeon can orient the vessel specimen in any natural anatomical orientation to have a similar tool and hand orientation as in the case of a real surgery.

It is capable of creating complex anatomical orientations encountered in anastomosis process. A flexible synthetic tissue strip is mounted on clips and oriented variously through an articulated arm. A series of preset orientations are calibrated to simulate various clinical patient postures and surgery sites. The cut edge of the synthetic tissue strip simulates a segment of the circumference of the vessel and synthetic tissue strip thickness simulates the thickness of the vessel wall. The tension on the synthetic tissue strip is adjusted to simulate the natural anatomical vessel and its floppiness. The sutured strip can be imaged and the regularity of placement of sutures evaluated much more accurately than when using a tubular structure.

The apparatus may be constructed as a portable device that can be placed in the field of view of a surgical microscope or used with a surgical loupe.

The apparatus may use two or more clamps to hold the tissue (latex, silastic tubes or natural body tissues). With clamps at two ends, the tissue is unsupported in the center where sutures need to be placed. It models the floppiness of an unsupported tissue. By having two clamps spaced apart for clamping opposed ends of the tissue, it simulates the situation of anastomosis where the tissue is held between clamps.

Placement of additional clamps can be added to simulate different aspects of anastomoses. For example additional clamps and orienting the tissue in a T fashion simulates end to side anastomosis. The tissue will have 4 ends in this case and the two pieces to be sutured together will form a 'T' shape.

In a further aspect the invention proposes a computer assisted algorithmic evaluation of the suture which is objective and repeatable.

Existing imaging devices such as mobile phones and surgical microscopes may be used as the image acquisition and transmission devices. To help the surgeon, a mobile application is used to guide the imaging process. Mobile application ensures clear and focused images are sent to the analysis system.

The system may be kept private, it may be confined to the training facility or it may be kept in the global public cloud. The system can be extended as a teaching tool by providing video of the procedures using correct techniques and video of procedures that result in defective sutures. Defective sutures are identified using the algorithmic evaluation.

The apparatus is positioned with tissue samples in a desired orientation, and suturing is performed. An image of the suture and the orientation of the device is sent to an analysis system using the image capture and transmission system. The received images are rated, either manually or automatically and based on the rating and complexity of the procedure, the images are ranked. A surgeon who performs the specific surgery is given the score correspond to the suture image uploaded by the surgeon. Surgeons can enroll into one or more study groups who perform specific types of practices.

A large number of samples from a large number of surgeons may be collected and analyzed. It provides enough data samples to quantify the errors that training surgeons make into suturing vessels. By capturing the video of the actual surgery and analyzing the hand movements or tool movements, the errors may be correlated with a specific type of hand movement or tool movement, hand or tool position and orientation, a tool grasping technique or a combination of these.

Further, the system can also provide a test platform for new suturing and knot tying procedures. By measuring the completion time, suturing quality and the learning time, the merits of the new surgical procedure can be quantitatively specified. By comparing with actual training data over a large population of training surgeons, the new procedure can be effectively qualified as a replacement for another type of procedure.

In a first specific expression of the invention, there is provided an apparatus as claimed in claim 1. In a second specific expression of the invention, there is provided a method as claimed in claim 10. In a third specific expression of the invention, there is provided a suture training system as claimed in claim 15.

BRIEF DESCRIPTION OF THE DRAWINGS

The present disclosure is illustrated and described herein with reference to the various drawings, in which like reference numbers are used to denote like system components/ method steps, as appropriate, and in which:

FIGS. 2(a) to 2(d) are views of the microtrainer training apparatus in FIG. 1 oriented to have the tissue in the horizontal plane.

FIG. 3(a) is an alternate implementation of the microtrainer training apparatus in FIG. 1 with 3 degrees of freedom for the tissue holder.

FIG. 3(b) is another alternate implementation of the microtrainer training apparatus in FIG. 1 with 4 degrees of freedom.

FIG. 3(c) is a perspective view of the arm in the microtrainer training apparatus of FIG. 1.

FIG. 18 is a flow chart of pre-processing an image of a suture.

FIG. 19 is a plan view of a suture on a synthetic tissue strip.

DETAILED DESCRIPTION OF THE DISCLOSURE

Anastomosis is the process of establishing communication between two streams, for example, blood vessels or leaf veins. Anastomosis may be defined as the natural, surgical, traumatic, or pathological formation of an opening between two normally distinct spaces or organs. In the human body, natural anastomosis recombines vessels that have previously been branching out. For example, arterial anastomosis establishes the communication between the arteries, or branches of arteries. Palmar arches, plantar arch, circle of Willis, intestinal arcades, labial branches of facial arteries are examples of natural arterial anastomoses. Venous anastomosis establishes the communication between the veins or tributaries of veins. For example, the dorsal venous arches of the hand and foot. Arteriovenous anastomosis (shunt) establishes the communication between an artery and a vein.

Similar to natural anastomoses, surgeons synthetically establish communication between vessel parts that are disrupted due to trauma. Surgeons perform anastomosis (stitching two tubular three dimensional structure) to permit vascular perfusion, nerve repair, during surgical procedures. For example, crossing anastomosis of a nerve is an effective method to treat peripheral and central nerve injuries. Anastomosis is usually performed by micro surgeons using specialized fine instruments on vascular and nerve structures of dimension 3 mm to 1 mm in diameter. The vascular and nerve structures are oriented in various planes in the body. Surgeons need to orient the surgical tools and their hands in various orientations to perform anastomosis. Surgical anastomosis consists of a sequence of fine moves.

In order to place a stitch, micro or macro, the needle ideally enters the tissue at 90 degrees, then the motion ideally follows the arc of the needle, so that the needle exits the opposite edge of the tissue ideally at 90 degrees to the surface. The path of entry and exit is ideally perpendicular to the cut. This relationship between tissue surface and needle ideally remains constant. When the orientation of the tissue is changed, the posture of the hands has to change accordingly to bring the needle and tissue in the correct relationship. This puts additional demands on the dexterity as the wrist, and fingers have a limited range of possible movements, i.e. forehand is the usual method for micro and backhand is significantly difficult. For example forehand stitch on left 45 degrees may be more difficult than placing a forehand in right 90 degree orientation.

Figure 1:
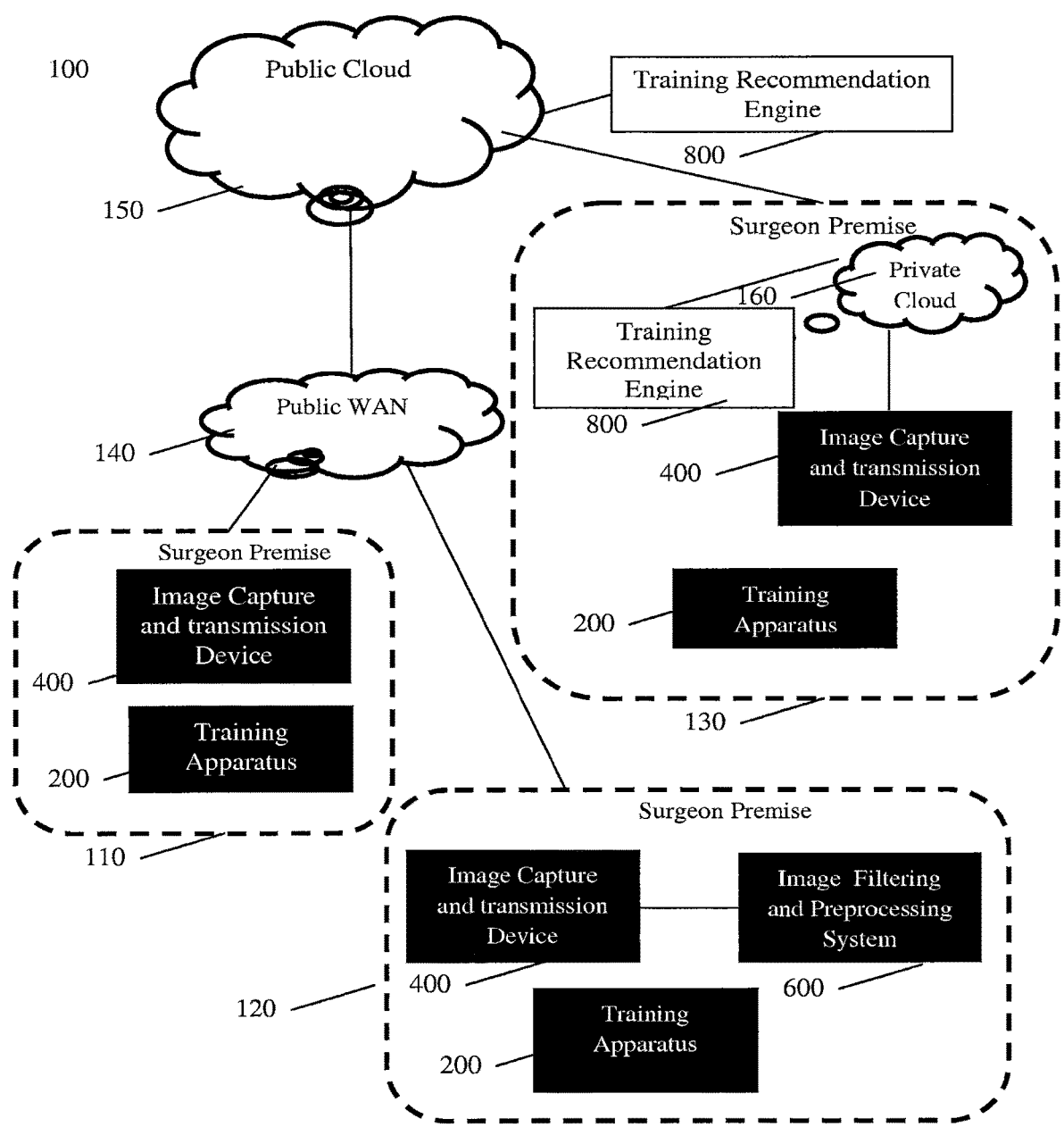
FIG. 1 is a block diagram of a suture training system according to a first embodiment of the invention.

In order to provide suture training, a system 100 is shown in FIG. 1 according to an embodiment. At each of three types of locations 110, 120, and 130 a suture training apparatus 200 is provided. Location 110 is a personal training location where the image acquisition and transmission device 400 transmits the data to the cloud 150 through the public WAN 140. In location 120 an imaging and image transfer device 400 sends an image or video of the suture to an image analysis system 600. It may compare the suture image features with the suture image features available in the Training Recommendation Engine 800 hosted in the cloud 150 through the WAN 140. In location 130, the training recommendation engine 800 is hosted in a private cloud 160. Location 120 is typical of a small surgery training facility such as a teaching hospital or a small surgery teaching facility. Location 130 is a typical multi-location dedicated surgery training facility which conducts regular surgery training courses. The image analysis system 600 may rate and/or rank the suture. Automated, semi-automated and manual rating may be provided to rate and/or rank the suture. The image analysis system 600 may also track the progress of the training. The image analysis system 600 may be located on a central server or provided in a cloud computing environment connected via a wired or wireless LAN, WAN or the internet. Training recommendation engine 800 has full functionality of an image analysis system 600 and additional video processing and ranking ability.

FIG. 2 shows an example of the suture training apparatus 200 according to an embodiment. A tissue holder 240 holds the simulated tissue. A supporting arm 230 has a first end 234 in clamp joint 250 with the tissue holder 240; and has a second end 232 in base joint 220 with a base 210. There can be an angle 204 in the supporting arm 230. Relative movement of the tissue holder 240 about the supporting arm 230 and relative movement of the supporting arm 230 about the base 210 allow adjustment of an orientation of the tissue with up to 6 degrees of freedom.

The base 210 can be fixed to a stable structure or a base platform (not shown). The base joint 220 together with the clamp joint 250 provides the necessary freedom of movement. Depending on the application, the base joint can be made with restricted freedom. The base joint 220 may be fixed as in 260 of FIG. 3(a) or provided with 1 degree of freedom as in 270 of FIG. 3(b). FIG. 3(a) provides an apparatus with 3DOF and FIG. 3(b) provides an apparatus with 4DOF. Other arrangements such as a hinge on the base joint are also possible depending on the requirements of the application.

The tissue holder 240 comprises a frame 244 with two clamps 242. The two clamps 242 are mounted parallel to each other on the frame 244 with enough space in between for suturing of the tissue sample. The synthetic tissue may be a latex strip 300, latex tube, silastic tube or natural tissue, such as chicken sciatic nerve, can also be used. The tissue is held between the clamps 242. The tissue is severed and unsupported at the center to simulate a severed or damaged anatomical vessel.

In another embodiment of the invention, the tissue holder 240 contains three clamps supporting two pieces of tissue, one with both ends supported through the clips and the other supported at one end. The free end is used for practicing end-to-side anastomosis. In yet another embodiment, the tissue holders may move independently.

The base joint 220 incorporates a socket 222 on the base 210 that engages a ball 224 extending from the second end 232. A ball-and-socket joint is thus formed for the base joint 220, allowing free positioning of the arm 230 in three degrees of freedom. The base joint 220 is constructed with sufficient friction for secure relative position of the arm 230 with respect to the base 210, which can be measured by markings 216. The base joint 220 maintains its position unsupported, unless subsequently adjusted.

The clamp joint 250 includes a socket 252 on the frame 244 engaging a ball 254 on the first end 234. Again a ball-and-socket joint is formed for the clamp joint 250 for positioning the tissue holder 240. This clamp joint 250 is also constructed with sufficient friction for securing the relative position of the tissue holder 240 with respect to the arm 230 unless force is applied to the arm 230 or the tissue holder 240 allowing for positioning of the two clamps 242 in any orientation with three degrees of freedom. A series of pre-set orientations may be used to simulate various clinical patient postures and surgery sites. Other joints or mechanisms may be provided to at least provide 3 degrees of freedom or 6 degrees of freedom depending on the requirements.

Other arrangements are possible. For example, the device may have a fixed base joint and a replaceable tissue holder and a fixed holder joint. The replaced tissue holders are in preset orientations. Here the joints may have zero degrees of freedom, but various oblique orientations are provided through multiple tissue holder arrangements.

Figure 4:
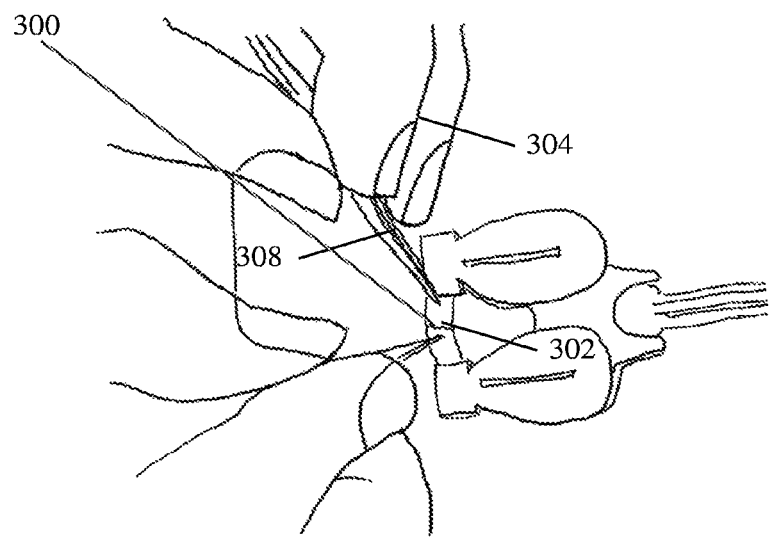
FIG. 4 is a sketch of using the suture training apparatus of FIG. 2.
Figure 5:
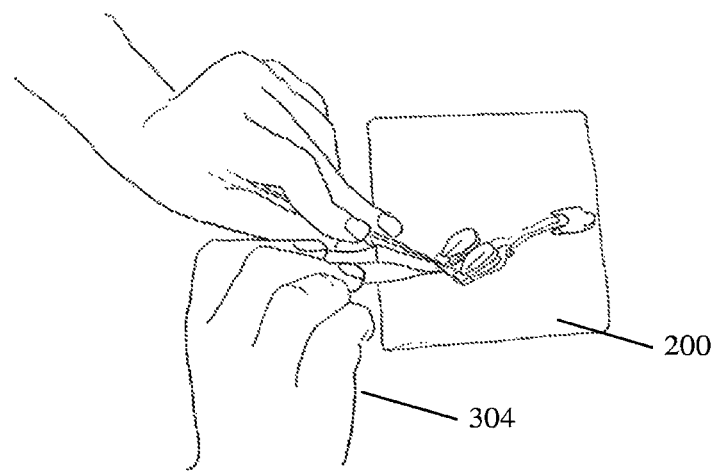
FIG. 5-10 are sketches of using the apparatus of FIG. 2 in various orientations.
Figure 6:
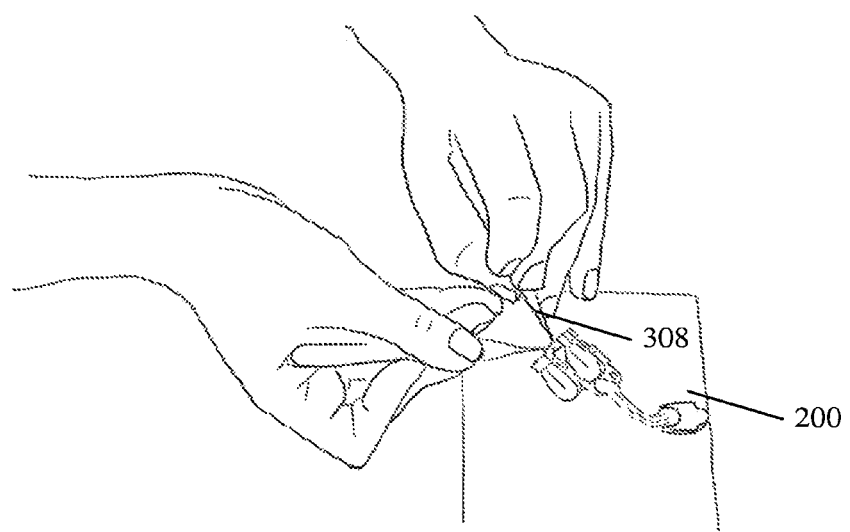
Figure 7:
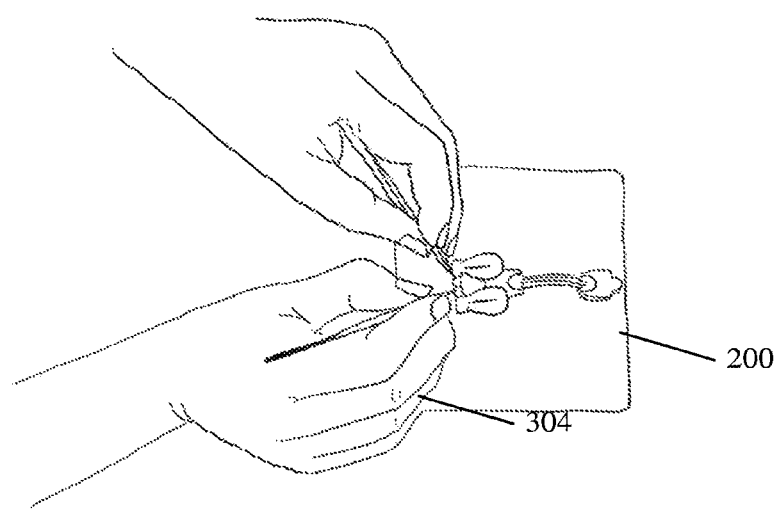
Figure 8:
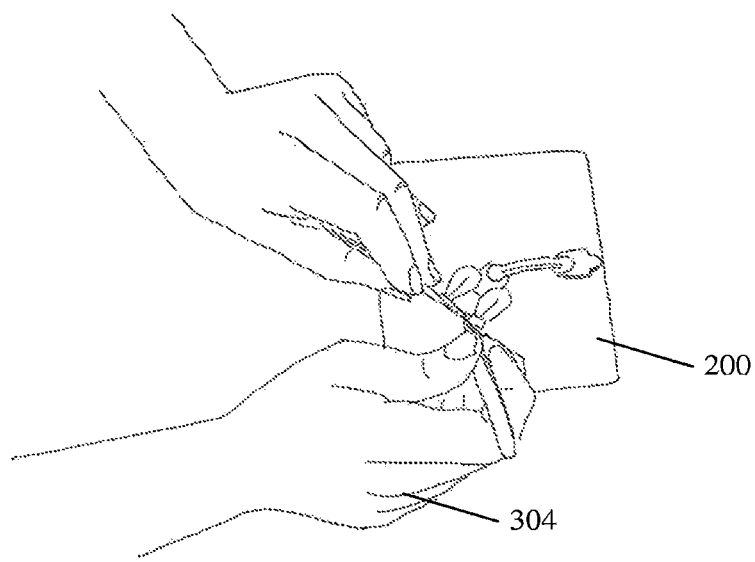
Figure 9:
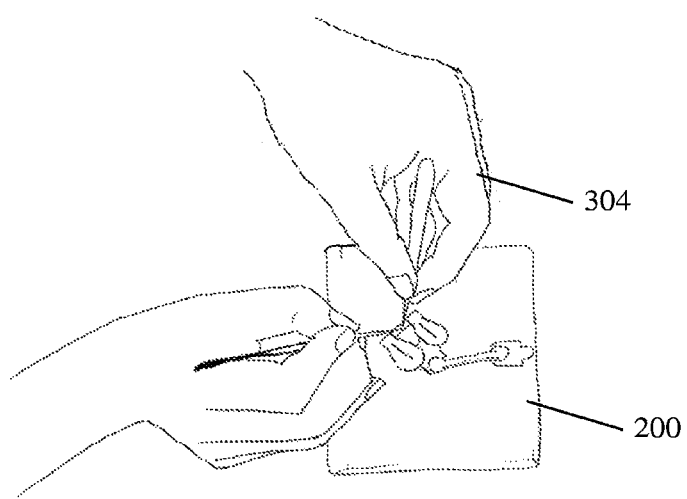
Figure 10:
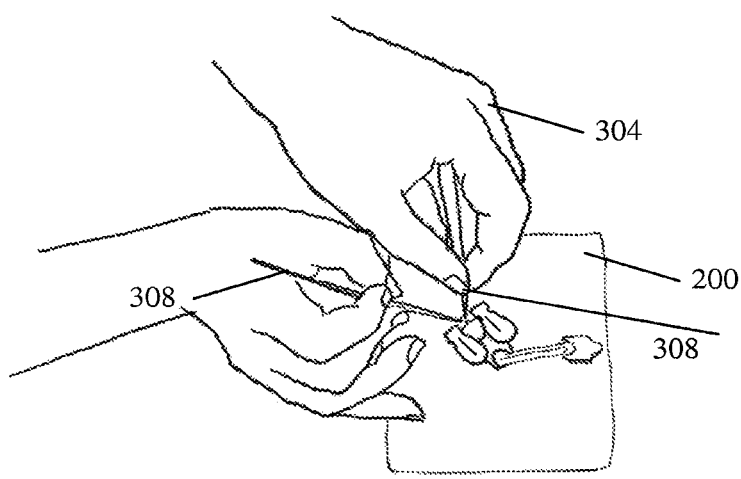

An example of the suturing process is shown in FIG. 4. A tissue strip 300 of suitable synthetic material such as latex (representing the tissue to be stitched) is mounted on the clamps 242. The clamps 242 with the mounted synthetic tissue strip 300 are positioned at the desired height and orientation by using the joints 220,250. The apparatus 200 is positioned under a microscope or magnifying device. The synthetic tissue strip 300 is severed 302 or otherwise damaged and the trainee 304 attempts to suture 306 the cut edges as accurately as possible with a tool 308. FIGS. 5 to 10 show the trainee 304 attempting to suture 306 the tissue strip 300 in a range of preset planes, which may allow an improvement in skills of suturing in different orientations.

The suture training apparatus 200 may be made of any suitable material, such as a thermoplastic rendering molding process, or may be made with materials such as wood, that can be machined to the desired form. The color of the apparatus is chosen to have good contrast under a microscope. The suture training apparatus 200 is preferably inexpensive and can be owned by each surgeon and surgery student. It eliminates the need for live animals or biological organs or tissues for training.

Figure 11:
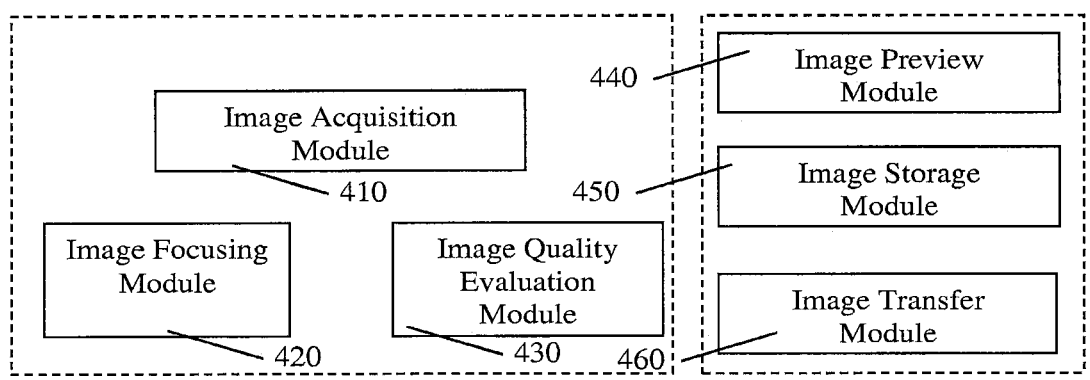
FIG. 11 is a block diagram of the image capture and transmission system in FIG. 1.
Figure 12:
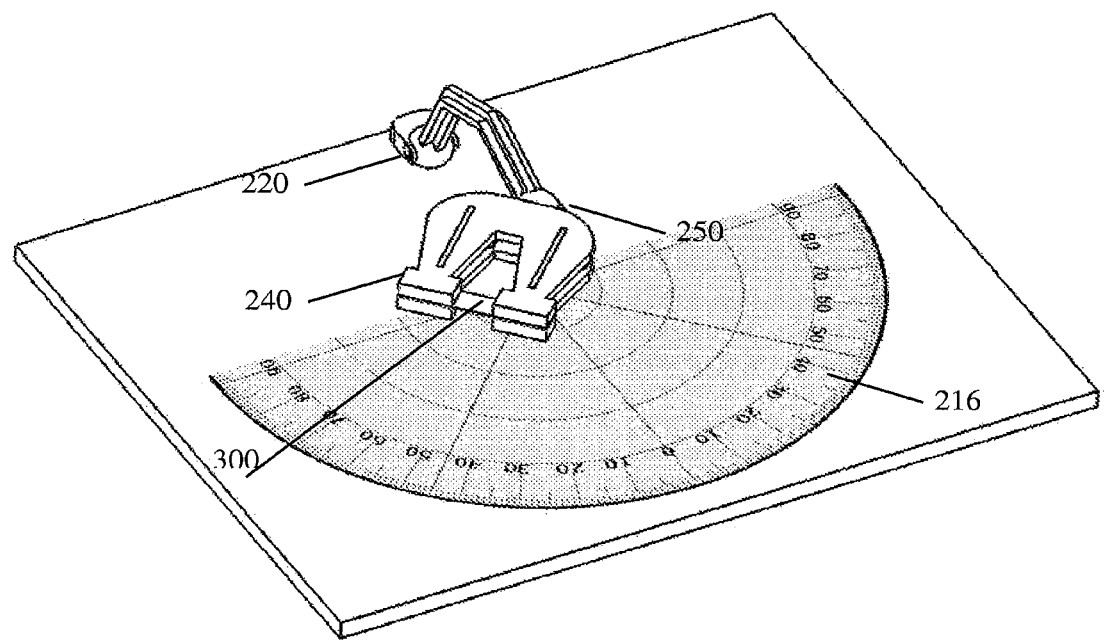
FIG. 12-17 are views of the apparatus of FIG. 2 in various preset orientations.

FIG. 11 shows an example of the image acquisition and transmission device 400 according to an embodiment. An Image acquisition module 410 includes a camera or other imaging device. An Image focus module 420 has the ability to focus the camera to obtain an orthographic view of the suture along with the suture holder. Image Quality Evaluation Module 430 assesses image quality by checking a histogram for contrast features and/or the ability to extract lines. Extraction of features may be used in devices with enough CPU power. For example, in mobile computing devices such as smartphones, the facility may be present.

The image preview module 440 helps to view the image before sending it for further processing and analysis. Images or poor quality may be discarded. It may also allow the surgeon to repeat the experiment if it is seen that the procedure did not go well. The image storage module 450 stores images captured by the image acquisition application for later transmission. This is useful to provide a preview of the images as well as to operate the image acquisition device without needing connectivity to the processing system or to the cloud.

Image transfer module 460 connects the transmission device 400 to the image processing system 600. The Image processing system 600 may be resident in the Image acquisition module 410, or in a separate computing device either deployed across the cloud 140 or offered as a local service. Adapting to the various deployment scenarios is achieved through the image transfer module 460.

Once the suturing is complete, a digital orthogonal image is acquired with the Image Acquisition Module 410. The Image Focus Module 420 may include: an imaging application which can detect the correctly focused suture image; a set of markings to measure the length of the suture and its orientation; a marking that gives the angular orientation of the device; and/or an imaging application that communicates with the analysis system to send focused images. The markings may be fiducial markings. The fiducial markings may include markings on the base and/or the joints to determine the location of the holder, markings to assist with locating or orienting of the holder, markings to measure the length of the suture, markings to measure the orientation of the suture, markings to determine if the imaging meets minimum quality, markings to determine the identity of the apparatus owner and other suitable markings.

An example of markings on the joints to determine the location of the holder, are shown in FIG. 3(c). The base joint markings 226 can be used to determine the yaw or pitch angle of the arm 230, or by geometry the height of the holder 240. The holder joint marking 256 can be used to determine the pitch or roll angle of the holder 240.

Figure 13:
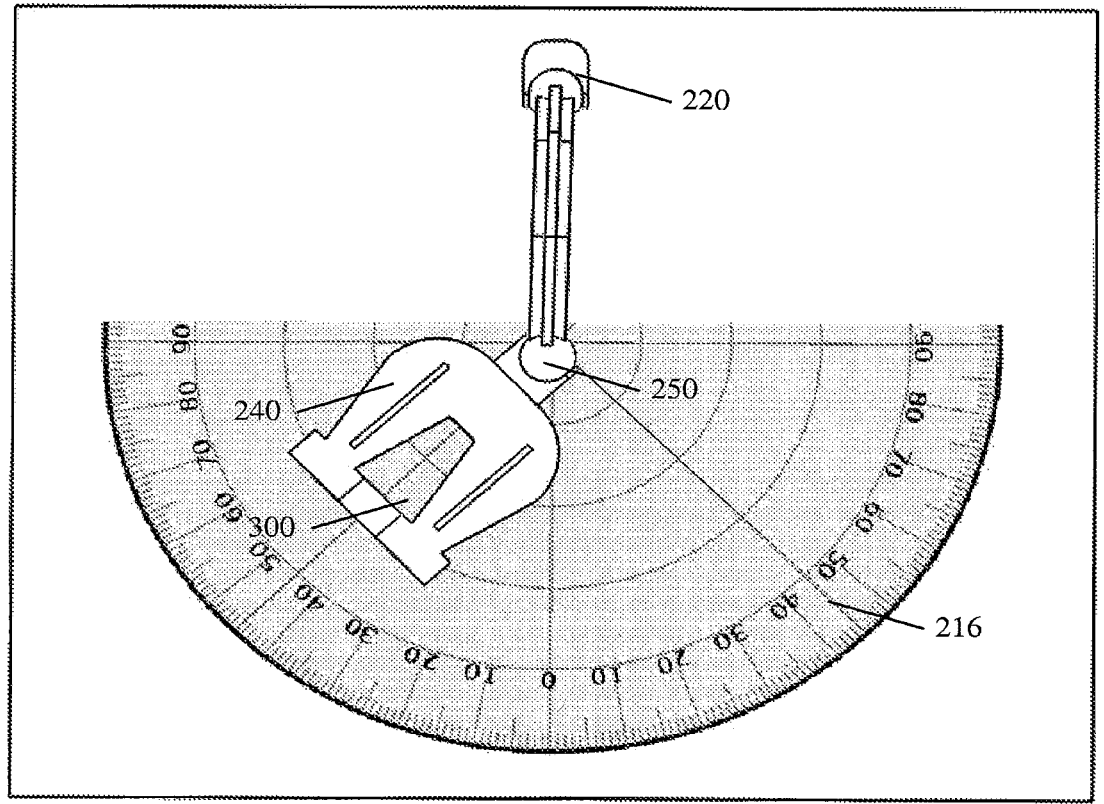
Figure 14:
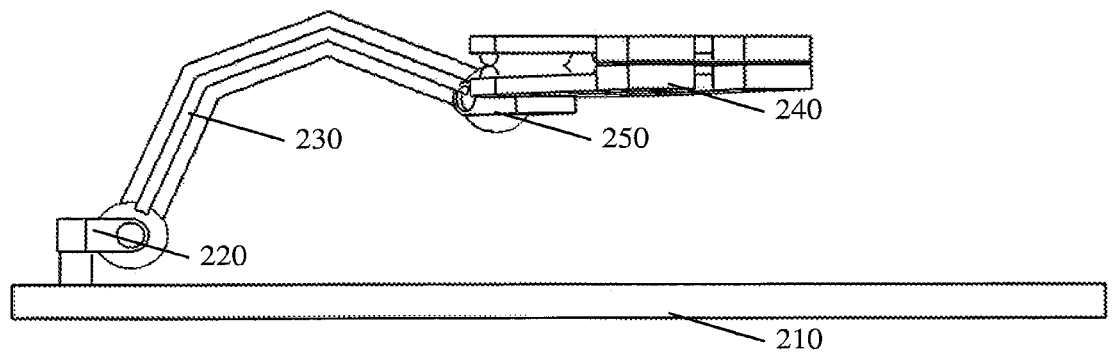
Figure 15:
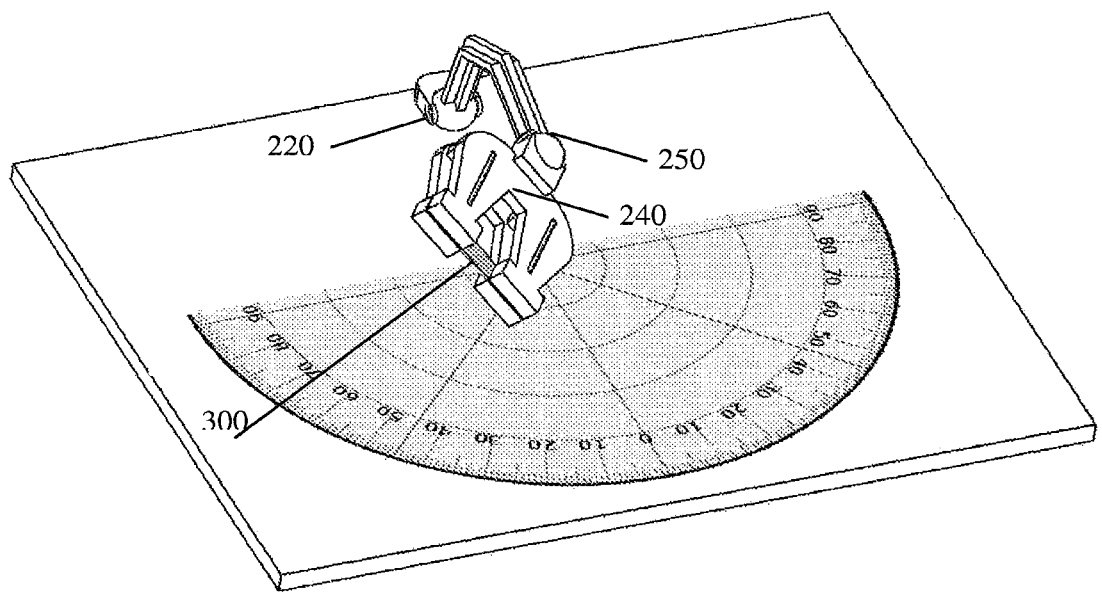
Figure 16:
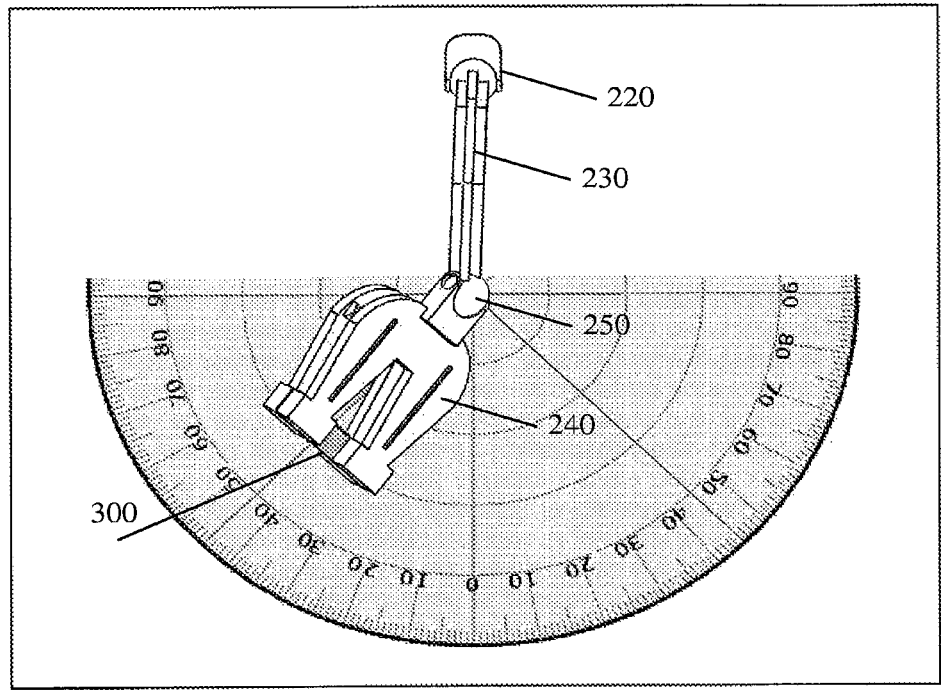
Figure 17:
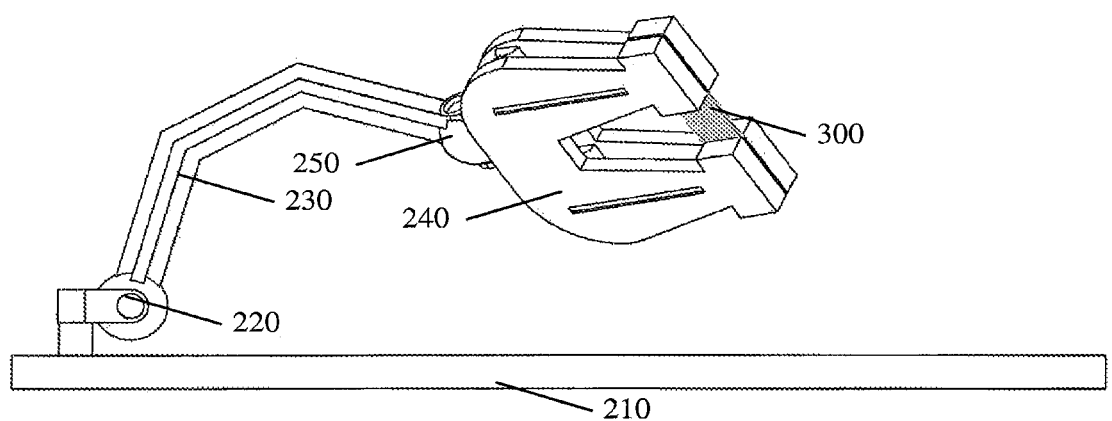

For example the fiducial markings may allow the user to orient the tissue in a range or preset planes as shown in FIGS. 12 to 17. In FIG. 13 the yaw angle scale on the base 210 shows the frame 244 is at a left angle of 45°. FIG. 14 shows the frame 244 is at a height from the base 210 measured by the base joint markings 226. In FIG. 16 the yaw angle scale on the base 210 shows the frame 244 is at a left angle of 45°. FIG. 16 shows the frame 244 is at a height from the base 210 measured by the base joint markings 226. FIG. 15 shows the frame 244 is at roll angle of 45° measured by the holder joint marking 256. Pitch angle can also be incorporated if the full 6 degrees of freedom are required to be trained.

The image capture process may involve a dedicated camera affixed in some way to the base 210. Alternatively a handheld camera or mobile phone may be used to take the images. The mobile phone may be a smart phone, for example, storing an application or "app" that is, written according to the phone platform or operating system. The application may include a camera interface which invokes and focuses the camera on the suture. The application may include visual or audible cues to help position the camera correctly for an effective image to be captured. Good focus may be determined when multiple lines are able to be detected in the suture image. Good focus may also be able to be determined based on the degree of blur in the image.

The Quality Evaluation Module 430 may be included in a software process 1400 to acquire suture images as shown in FIG. 18. The quality may be obtained by computing the contrast transfer or based on the features detected by the software. In some cases, both focus and quality may be determined by being able to read a bar-code added on the tissue holder. The process 1400 adjusts imaging parameters (step 1402), and acquires the image (step 1404). If the image is in focus (step 1406), the image quality is calculated (step 1408), and above the quality threshold (step 1410) then the image is stored (step 1412) and transmitted to the central image analysis system 600.

Another measure of quality is determined as follows. Let H(i) be the histogram of the image at intensity i, meaning the count of image pixels having intensity i. An intensity i is a peak, if H(i)>H(i−k) and H(i)>H(i+k) for value of k to a small integer such as 5. K is known as the width of the peak. Using these definitions, if the peaks in the histogram are determined to be three, then it is a tri-modal histogram, and the underlying image is trimodal. The image may be a tri-modal image with the three histogram modes occurring at the suturing device image portion, suturing tissue strip 300 and suture 306. All three of being distinct and can easily be contrasted. One quality estimate is based on the check whether the image is trimodal.

Another method is to check the relative size of the peaks. If i, j and k are the three peaks in the descending order of heights, then the ratios H(i)/H(j) and H(j)/H(k) are computed to evaluate the quality of the image.

Another method is to compute the Hough Transformation of the image. A Hough transformation considers the intensity edges in the image and records them. For example, a Hough transformation of the image classifies the image pixels to belong to a line by being proximal to the line and above a specified intensity threshold. A line is specified by using the perpendicular distance of the line with the origin (r) and the angle Θ that the line of length r makes with the positive x-axis. There are three pairs of markings on either side of the clip assembly. Each marking has two line segments forming a cross pattern. Two lines of the cross are perpendicular. The pairs of cross patterns on either side of the clip are similarly placed. In the Hough transform, there will be lines that are parallel to each other which will have the same angle Θ, but different values of r. Detecting these lines in the Hough Transformation of the image assures that the image is of good quality.

Figure 20:
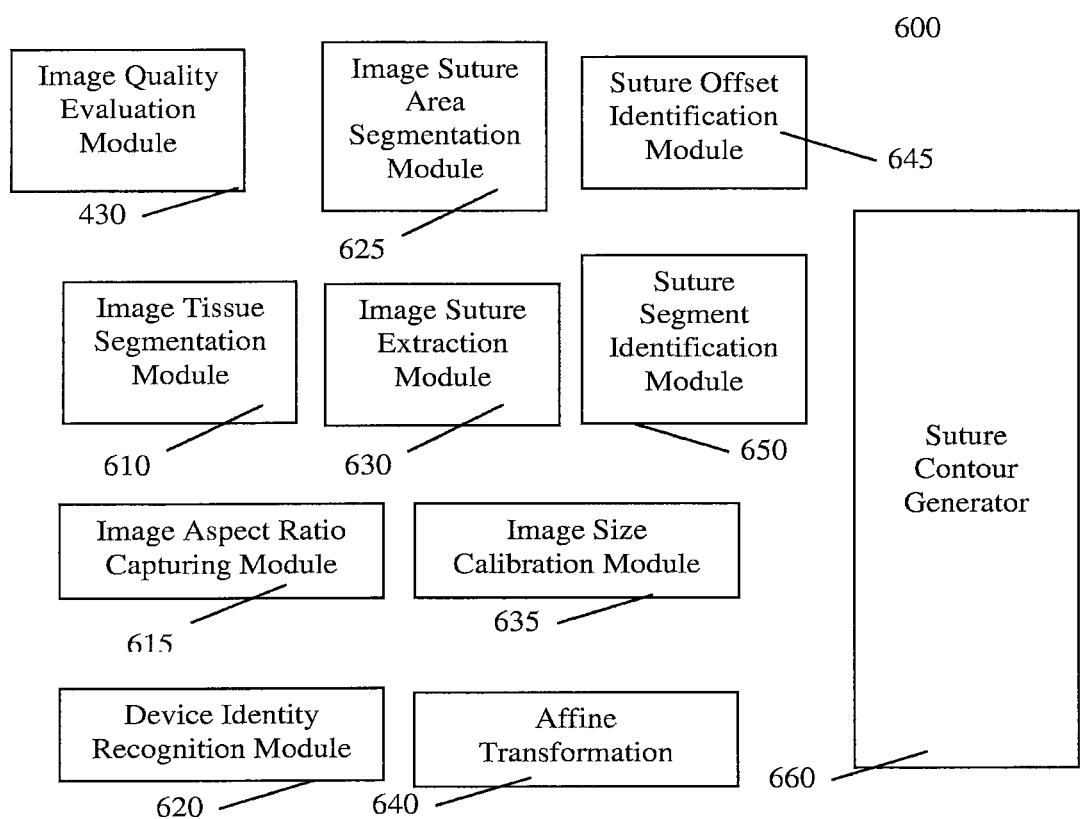
FIG. 20 is a block diagram of the image filtering and pre-processing system in FIG. 1 for manual and semi-automated and automated evaluation of suture images.

FIG. 20 shows an example of the image filtering and pre-processing system 600 according to an embodiment.

The Image quality assessment module 430 may be present in the image acquisition device 600 as well as on the processing device 400. Some high end devices may be capable of high quality processing, other devices may be limited. A full version of quality assessment may therefore be implemented in a central location. Image quality assessment is important for more accurate results in determining the quality of the suture.

The purposes of the image filtering and pre-processing system 600 may include assessing whether the image is of sufficient good quality and if it meets the quality requirements, enhancing the image for better processing and extracting features, such as the type of suture and the attributes of suturing, from the image.

To extract the image features, the region of interest, (the region, including the synthetic tissue and tissue holder) are extracted from the image by segmenting the image. A set of landmarks is identified; for example, the metal clips 248 of the tissue holder may act as a reference point. There are two segmentation modules, the Image Area Segmentation Module 625 which detects the area of an image which contains the synthetic tissue, fiduciary markings 246 and the tissue holder and the Image Tissue Segmentation Module 610 which extracts the minimum rectangle containing the synthetic tissue and the suture. Instead of using a single segmentation, the use of multiple segmentation modules with different heuristics may increase accuracy in a wider range of scenarios.

The Image Aspect Ratio Capturing Module 615 is used to present the region of interest in a non-distorting magnification by enforcing a common aspect ratio for the region of interest. The Image Size Calibration Module 635 is used for converting the image dimensions in pixels, in the actual physical object dimensions in millimeters or fractions of millimeters.

Each device has a coded marking that indicates the device ID. Device ID is one of the targets of the segmentation. The Device Identity Recognition Module 620 uses the coded markings to identify and decode the device ID.

In a segmented image, special features are expected to be present. For example, while lines may be present in other parts of the image, the lines present in the synthetic tissue are highly likely to be the sutures. The segmentation operation, thus reduces the detection errors that could be caused by the automated image processing. The Suture Offset Identification Module 645, identifies the offset 340 of the sutured tissue ends. There may be one or two offsets based on the type of suturing defect. Image suture extraction Module 630 extracts the image coordinates of the suture knots 320 from the suture image. If the suture image cannot be extracted, it Module 630 will extract the area containing the suture and present it for manual extraction of suture knots by the human user, albeit marking the suture knot coordinates. Suture Segment Identification Module 650 combines topographically adjacent suture knots 320 to form suture segment 310. Each suture segment is measured for length. Suture Contour Generator 660 determines a line of best fit through the suture knots and can be used for assessing regularity.

The Affine Transformation 640 is a utility module used by other modules to transform the image.

In general terms there are two main filtering preprocessing operations, (i) extract the image features and (ii) derive the suture quality and rank to yield a recommendation. Suture features may be extracted by identifying the segment and offset lengths and converting these lengths into physical coordinates. For the conversion of the pixel (image) coordinates to physical coordinates, reference objects such as the metallic clip on the holder, clip holder width, fiduciary markings may be used.

The suturing practice may also be video recorded to capture the surgical motion. The video is analyzed frame by frame to detect motion and produce the movement. The recording should be done through the help of the microscope used in the practice.

The grading process may be carried out automatically, semi-automatically or manually with a Suture Image analysis System. The system may include: an analysis system that can analyze images and detect suture defects and extract procedure complexity level; a rating system that grades the suture based on the defects or lack of thereof; and/or a ranking system that can rank the images across a collection of rated images and the procedure complexity.

The image is stored by the central image analysis system 600 with software installed to process each image automatically, semi-automatically or manually. First the entry and exit points of the sutures are identified, as well as the tissue edge junction while visually displaying the image. The user is then able to use the software to estimate inter-suture distance, angle of the suture and statistics summarizing the quality of the suture. The results are displayed in a tabular format on the screen and can be printed out.

The evaluated suture images are available only to the registered users. In some cases, a registered user will have a device ID. In some configurations, the device ID is bar coded on the tissue holder and is read using the image. A user is required to present the matching device ID when accessing the suture images. A device ID may be shared by multiple users. In other configurations, a registered user will have an organization's identity and multiple training devices are registered with the organization.

Figure 21:
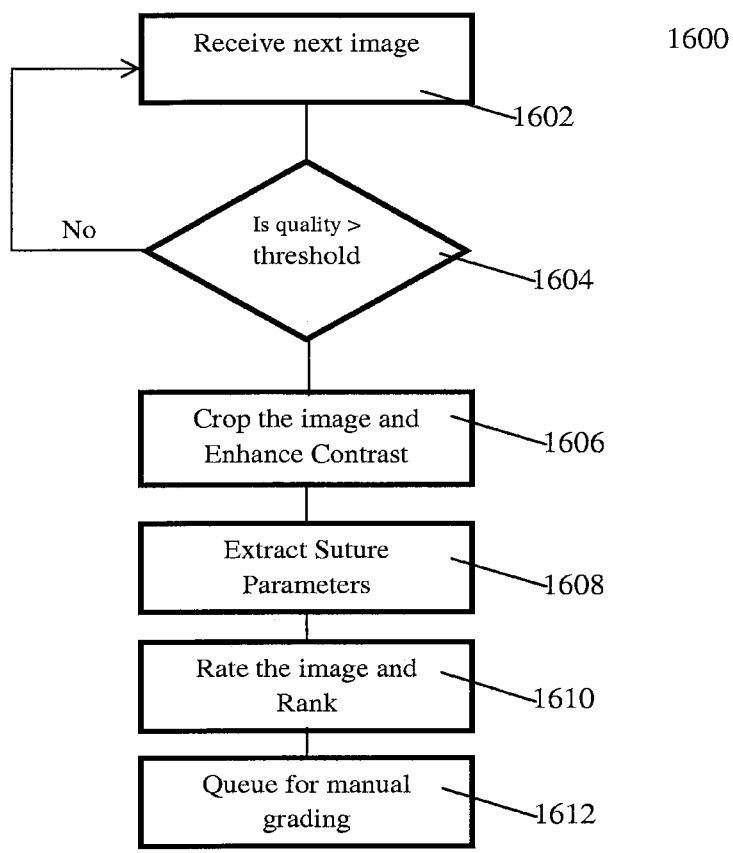
FIG. 21 is a flow chart of grading a suture.

The system also has a software program 1600 that visualizes the digital image of the synthetic tissue strip and allows processing on the image to automatically or semi-automatically detect suture entry and exit points as well as the tissue edge junction as illustrated in FIG. 21.

The suture is evaluated using a single image of the suture. The image of the suture is acquired and transmitted for grading the suture 1602. The grading system first processes the images to improve the visual clarity to be examined by the automated process or through a manual process 1604. In the next step, it crops the image to reduce the size of the image 1606. The cropped image will have the suture and the clip assembly in the image. The cropped image is stored for processing by the automated software agent or by the manual grading or a combination of both.

Alternatively the suture may be evaluated using multiple images or videos of the suture. Images may be taken from different viewpoints to extract a 3D or a pseudo 3D representation of the suture. For example an image may be taken from the front side of the suture and the back side of the suture. This may be useful for more accurately measuring certain features e.g.: evertion.

In the automated process, the suture is evaluated to derive the suture distance, the distance of the suture entry and exit points in relation to the wound, the appearance of the wound surface 1608. The rated suture may be ranked 1610 according to stored data or queued for manual grading 1612.

In automated grading, the lines are extracted using one or more of the following methods. Lines may be extracted using the filtering methods, for example, using a Sobel operator or Canary Filter. A filtered image having lines of, for example, suture, holder assembly, tissue edges, are subjected to line evaluator.

One approach to do line evaluation is using the Hough Transform to transform the image into a histogram of lines of varying r and $\Theta$. From the r values, the lines corresponding to suture images are heuristically picked. For example, the suture image is situated between the lines of the holder assembly. It is also placed between the cross markers on the holder assembly. Hence the r values must be between the lines corresponding to the right and left holder assemblies. The $\Theta$ values can be very varying depending on the way the suture lines run.

Once the suture area is located using the line, histogram given by the Hough Transform, a small area of the image corresponding to the suture is subjected to the processing. The suture 306 is composed of eight suture segments 310 as shown in FIG. 19. An ideal suture will have each segment is about the same length. For example, by placing a 4 mm wide latex specimen across the tissue holders, divided and sutured, there should be 9 suture knots 320, each marking an end of a suture segment 310.

Good suturing involves regular 0.5 mm spacing (clamp width is 4 mm, a 4 mm strip is recommended for use), and the trainee 304 should be able to place 7 to 8 evenly spaced sutures 306. Suture bite should be symmetrical on both sides of the cut edge and the edges should be everted not inverted. The degree of eversion/inversion, the pitch and its regularity forms the basis of the quality index. For example, in one method, the degree of eversion is calculated as the height inferred by the shading of the image. In other cases, the width of the suture line is treated as the degree of eversion. By calculating the distance between the entry points and exit points, the regularity of the entry and exit points are calculated. For example, the entry points may be at a pixel distance of 20 pixels apart on average and the maximum deviation of the entry point distance may be 2 pixels and is treated as having good regularity compared with one having a maximum deviation in the entry point distance of 5 pixels.

A good suture should be regular as well as be everted. One method to check whether the suture 306 is regular is to locate the suture knots 320 and grade the suture segments 310. Based on the types of errors that may be made, a suture 306 is considered as comprising eight suture segments 310 and two offsets 340 at either end of the suture segments 310. If offsets 340 are present, then the suture 306 is not done correctly. If each of the suture segments 310 are of a specified length (4 mm into 8 segments gives each segment to be of 0.5 mm in size which may be graded for variation in segment length from 0.5 mm) then the suture is done perfectly.

In the manual grading process, the image is moved to locate the suture area into focus. Then a set of reference points is selected to create the measurement units corresponding to the image pixels.

In one method, the distance between the ends of the clip holder is treated as a reference. The width of the clip holder is about 5 mm and accordingly, the pixel dimensions may be made. In another approach, the distance between the cross patterns on either side of the clip holder assembly may be taken. There are multiple distances that could be used as reference.

Once the reference points are marked, region of interest is marked to include the suture area. The image is then magnified with the suture area alone. Then the offset if any is marked. An offset arise if there is a mismatch between the two ends of the tissue being sutured. At most two offsets can occur. Then the suture knots are marked to show the suture segments. The system calculates the segment distance.

At the end of the grading, a colored ribbon with 10 segments is produced, two segments for the offset errors and 8 segments for the suture segments.

In Semi-automatic Grading mode, the system helps to identify the region of interest and points of interest such as the suture knots, holder assembly ends, suture markings. The manual grader may augment these identified points and extract the 8 sutured segments and offset errors. The offset may be marked as the difference between two tissue ends in the suture. In some sutures there will be no measurable offset on either end of the suture and in some there is offset in one end of the suture and in others there are offsets on both ends of the sutures. In both manual and semi-automatic modes, the grader may award bonus points for evertion.

A Scoring Algorithm may be applied to the image to provide a score of the suture of the image. Using one of the methods (manual, automatic or semi-automatic) methods, the suture is extracted into a graded ribbon representation. There are typically 10 segments in the ribbon, 8 segments for the suture and 2 segments for the offset. The scoring algorithm examines the ribbon and assigns scores for each segment.

In one method of the scoring algorithm, the scores are computed as follows, where O1, O2, S1, S2, . . . , S8 represent the ribbon segments.

Score($Si$)=max(10−|(length($Si$)−0.5 mm)|*2.0,0)

Score($Oi$)=10 if length($Oi$)==0[0100]Else min(0,−length($Oi$)*2.5)

Total Score=sum(Score($Si$)) for $I$=1 . . . 8+sum (Score($Oi$)) for $I$=1 . . . 2

Another implementation of the algorithm considers the standard deviation across length of segments. For example, if the segments are {0.6, 0.5, 0.4, 0.6, 0.7, 0.4, 0.5, 0.3}, then the standard deviation of the segment lengths is calculated by calculating the mean and finding the sum of squared deviations from the mean. Based on this, each segment may be given a score based on the closeness to the standard deviation. For the above example, the mean is 0.5 and standard deviation is 0.130931. Hence segments with length 0.3 and 0.7 will be punished in the scoring.

In yet another implementation, the value of the standard deviation itself is taken as a score.

The scoring scheme may also be augmented using minimum number of segments needed to consider a valid suture. For example, a suture with less than 4 segments is scored as zero.

Figure 22:
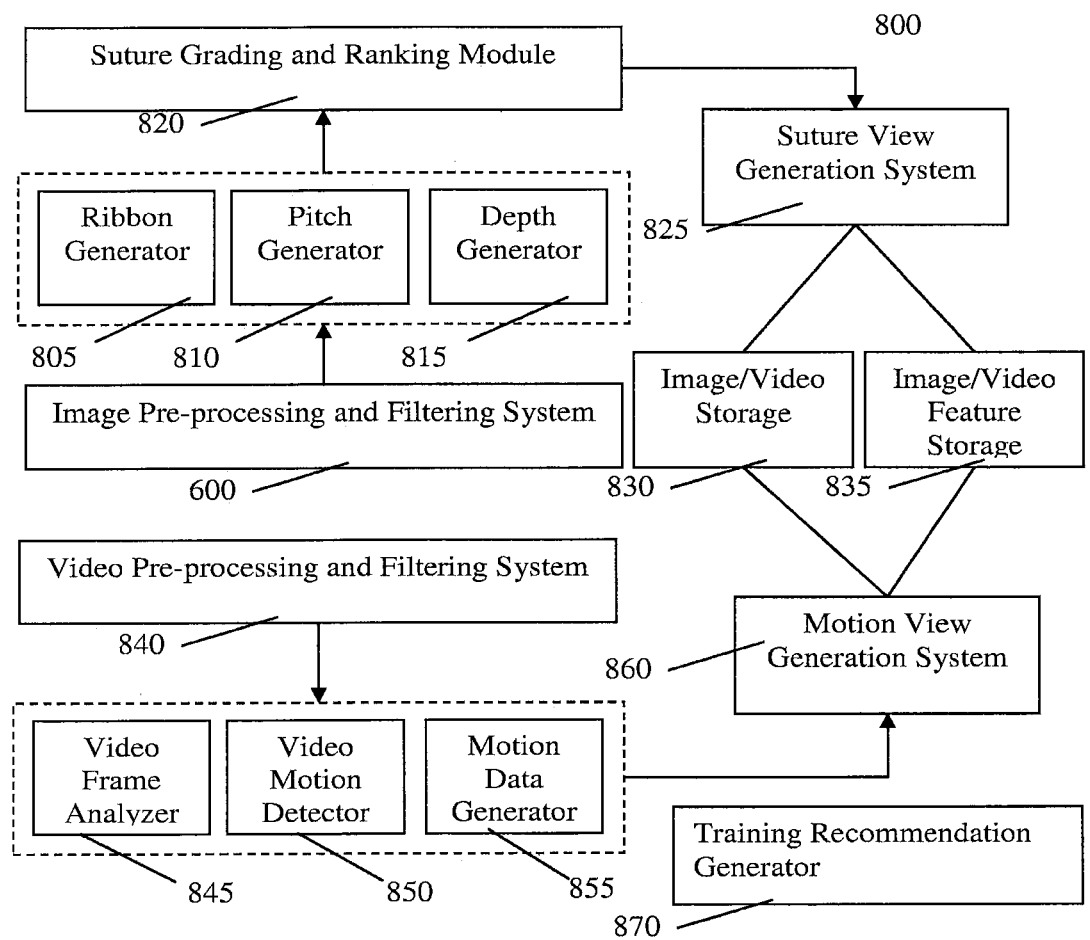
FIG. 22 is a block diagram of the components of training recommendation engine in FIG. 23 is a flow chart of training recommendation process.

FIG. 22 shows an example of the Training Recommendation Engine 800 according to an embodiment. The Training Recommendation Engine 800 may include a reporting system that keeps the progress of a surgeon over time and indicate the progress; a grouping system that can match and pair surgeons with complementary skills to develop the skills of both; and/or a video indexing system that can index suture defects to videos explaining suturing defects and remedy. After obtaining the suture quality in terms of the segment lengths and offsets, it may be correlated to suturing techniques. Techniques that give better precision are recommended. A ribbon representation of the suture is produced for easier visual comparison between training sessions.

The Ribbon Generator 805 may generate set of lengths from a sequence of pixel coordinates indicating suturing knots, and apply the scoring algorithm to create a color coded strip. The ribbon generator 805 provides input to a Suture View Generation System 825 to provide a rectangular image corresponding to the suture with the number of rectangles equal to the number of segments in the suture.

The Pitch Generator 810 determines the regularity with which the sutures are made. The Pitch may be the mode (most common) of the segment lengths. Each segment length may be matched to one of four segments 310 sizes and the most common segment size is used as the output of the pitch generator 810.

A Depth Generator 815 processes an area of the image and determines the maximum depth of the area by comparing the pixel intensity variation across the area, while maintaining continuity between the adjoining regions.

Suture Grading and Ranking Module 820 grades the suture based on the rectangular image, pitch and depth. Rated suture images are compared with other suture images to produce a ranking order. A composite score may be assigned to the images based on the output of the Ribbon, Pitch, Depth generators 805,810,815 and the images are sorted according to the non-increasing value of the score.

The Suture View Generation System 825 produces a suture view by superimposing extracted features on the extracted suture image. The superimposed features may include the regularity of the suture segments, the composite score and rank of the suture, a visual ribbon representation of the suture and markings to show suture knots.

The generated view of the image is cached or stored for each given suture using two storage facilities in the Training Recommendation Engine 800. The Image/Video Storage 830 is for image and video pixel data storage and the Image/Video Feature Storage 835 is for the extracted data. The Image/Video Storage 830 contains the original image as well as images obtained using various segmentation modules. The Image/Video Feature Storage 835 contains data such as the ribbon data, the pitch data, the depth map, and other associated information such as the time taken to perform the procedure, the training device used in the procedure, the orientation of the device during the procedure.

The training Recommendation Generator 870 includes image preprocessing, feature extraction and user view generation. A recommendation of a procedure is generated by the system based on the analysis of the movement. Surgical movement data is analyzed using three video analysis components.

The Video processing and filtering system 840 processes individual video frames for quality and assess the frame delay. It converts the video into a sequence of images that can be analyzed using the image processing and filtering system. The module focuses the video segments on the microsurgical movements.

The Video Frame Analyzer 845 segments the frame into object landmarks which are assessed for movement in subsequent frames. For example, the location of the tip of the needle or the needle holder may be identified in each frame.

The Video Motion Detector 850 is used to detect movement of objects identified by the video frame analyzer 845. The movement is tracked across each frame of the video data.

The Motion Data Generator 855 determines coordinate data of object movement across frames. This can be used to approximate the surgical motion.

The Motion View Generation System 860 produces a view of the surgical motion from the motion data generator 855 to a workspace. The surgical motion may be restricted in a small bounding cube of surgical movements. This view data may be used in rating or ranking to compare to other training data (or idealized motion data), it may be used in explaining motion errors to the trainee or it may be used in identifying peers.

Figure 23:
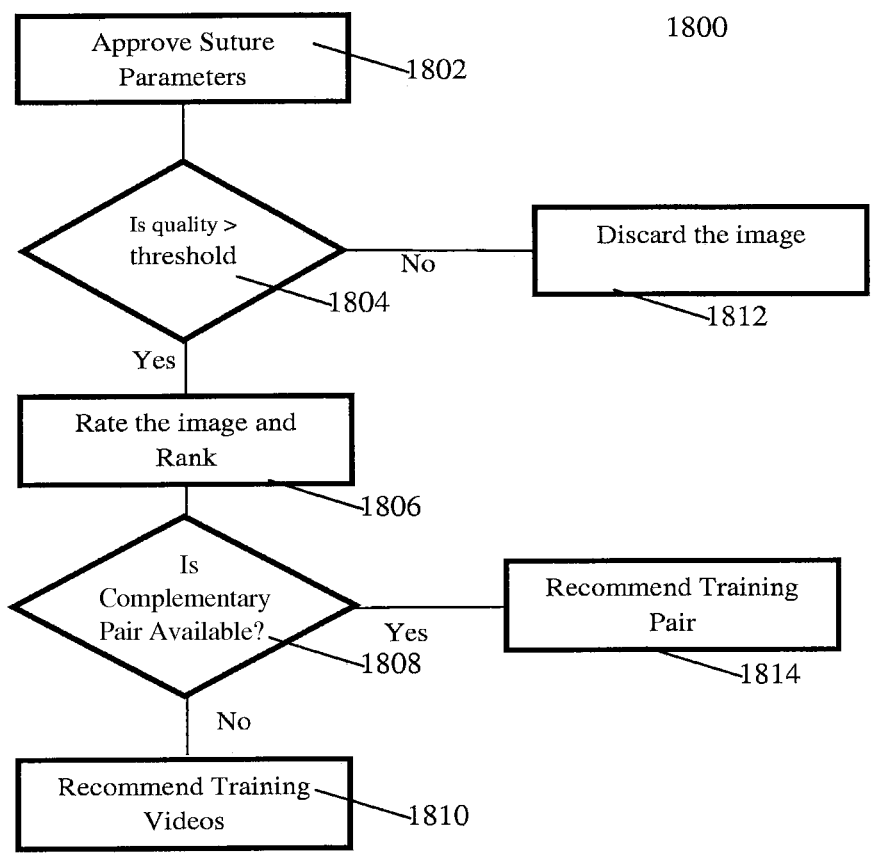

As shown in FIG. 23, the training recommendation engine 800 may execute software 1800 that approves suture parameters (step 1802), checks if the quality is above a threshold (step 1804), rates the image and rank (step 1806), checks if a complimentary pair is available (step 1808), and if not, recommends training videos (step 1810). If the quality is below the threshold (step 1804), the image is discarded (step 1812). If there is a complimentary pair available (step 1808), a training pair is recommended (step 1814). The Suture View Generation System 825 allows viewing the suture images with the ribbon representation of the suture. The ribbon representation uses color codes and ribbon lengths to give a summary feedback to the practicing surgeon. In one implementation of the ribbon coding, a perfect suture has 8 green segments of equal size and two offsets on either side with zero size. The equal sized segments may be colored green, for example. Other encoding schemes are possible.

A non-perfect ribbon will have different sized (lengthwise) segments that are variously colored. Some ribbons may have fewer than 8 segments and some may have more than 8 segments. There may be non-zero sized offset segments as well. By examining the segments, a one-to-one mapping between the segments and the image is provided. For example, by hovering over the segment, a corresponding portion of the suture is highlighted. Hence the surgeon will be able to analyze the errors in his suture using the recommendations provided in the ribbon.

The Training Recommendation Engine 800 may use the ribbon to find surgeons who have complementary errors, and recommend peering for improving the techniques of both the surgeons. By storing the training data over the days, the progress of the surgeon is monitored; for example: whether the errors are reduced over the training period. Two types of graphs are used to give feedback and recommendations to the surgeon. The score of the surgeon over the period of the training and individual points of the training. When individual points are examined, the surgeon can see the image with the ribbon annotation.

The surgeon is also provided by the segment length over time for each of the eight segments. The segment lengths of individual segments may correspond to a specific skill in suturing.

Whilst exemplary embodiments have been described in detail, many variations are possible within the scope of the invention as claimed as will be clear to a skilled reader. East embodiment may be independent and not necessarily used with the other embodiments mentioned. For example a fixed inclination latex strip holder may be inserted into a base with a vertical slit. This holder may then be used with the imaging system and/or suture recommendation engine. In a further alternative, the rating system may compare the image against candidate good sutures. After aligning both the patterns to have the same starting point, the variance can be determined to compute a rating.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

What is claimed is:

1. A system of microsuture training, the system comprising:
   a suture training apparatus configurable with simulated tissue to simulate natural anatomical tissue encountered in actual surgery;
   an image analysis system configured to receive a video of a suture performed using the suture training apparatus and the simulated tissue;
   a feature extraction system configured to extract physical features of the suture from the video;
   a suture grading system configured to score the suture based on the extracted physical features of the suture and based on a rating and complexity of the suture to determine a quality of the suture in an objective manner;
   a recommendation engine configured to recommend training based on the quality and the extracted physical features; and
   a movement tracking system configured to track hand or tool movements from the video based on a plurality of fiducial markings on the suture training apparatus, and based on the hand or tool movements, identify errors selected from the group consisting of: hand or tool movement, hand or tool position and orientation, tool grasping technique, or a combination thereof,
   wherein each of the image analysis system, the feature extraction system, the suture grading system, the recommendation engine, and the movement tracking system is executed on one or more servers, and
   wherein the plurality of fiducial markings include fiducial markings on a base of the suture training apparatus providing an angle of a holder of the suture training apparatus relative to the base and fiducial markings on joints of the suture training apparatus providing (1) yaw or pitch of an arm of the suture training apparatus and (2) pitch or roll of the holder.

2. The system of claim 1, further comprising a local database of suture images, suturing motion elements, and training recommendations communicatively coupled with a plurality of image analysis systems, wherein the suture grading system is configured to rank the sutures based on a plurality of databases.

3. The system of claim 1, wherein the feature extraction system, the suture grading system, and the recommendation engine are implemented in a cloud.

4. The system of claim 1, wherein the physical features are extracted by generating a ribbon representation for each of a plurality of segments of the suture, and
   wherein the quality of the suture is scored by comparing a length of each of the ribbon representations with a predetermined optimal length or by calculating a standard deviation of the lengths of the ribbon representations.

5. The system of claim 1, wherein the suture is scored by determining a degree of eversion of tissue, determining a pitch of the sutures, determining a regularity of the sutures, determining a location of knots, and determining if alignment errors are present.

6. The system of claim 1, wherein the physical features are extracted by identifying a plurality of segments of the suture, measuring offset lengths of edges of simulated tissue, converting the offset lengths into physical coordinates, and determining image coordinates of suture knots of the suture.

7. The system of claim 1, wherein the quality of the suture is based on spacing of the suture, symmetry of the suture, degree of eversion/inversion, pitch, and offset of tissue.

8. The system of claim 1, wherein the suture training apparatus is configurable with a plurality of orientations of the simulated tissue, wherein the plurality of orientations are objective based on one or more fiducial markings on the suture training apparatus.

9. The system of claim 8, wherein the rating and complexity of the suture are based in part on an orientation of the simulated tissue when the suture was performed.

10. A method of microsuture training, the method comprising the steps of:
    providing a suture training apparatus for use by a trainee, the suture training apparatus configurable with simulated tissue to simulate natural anatomical tissue encountered in actual surgery;
    receiving a video of a suture performed using the suture training apparatus and the simulated tissue;

extracting physical features of the suture from the video;

scoring the suture based on the extracted features of the suture and based on a rating and complexity of the suture to determine a quality of the suture in an objective manner;

recommending training based on the quality and the extracted physical features; and tracking hand or tool movements from the video based on a plurality of fiducial markings on the suture training apparatus, and based on the hand or tool movements, identifying errors selected from the group consisting of: hand or tool movement, hand or tool position and orientation, tool grasping technique, or a combination thereof or identifying preferred movements in surgery, wherein the plurality of fiducial markings include fiducial markings on a base of the suture training apparatus providing an angle of a holder of the suture training apparatus relative to the base and fiducial markings on joints of the suture training apparatus providing (1) yaw or pitch of an arm of the suture training apparatus and (2) pitch or roll of the holder.

11. The method of claim 10, wherein the step of extracting physical features comprises extracting the suture into a graded ribbon representation having a plurality of ribbon segments, and
wherein the step of scoring the suture comprises comparing a length of each ribbon segment with a predetermined optimal length or calculating a standard deviation of the lengths of the ribbon segments.

12. The method of claim 10, wherein the step of scoring the suture comprises determining a degree of eversion of tissue, determining a pitch of the sutures, determining a regularity of the sutures, determining a location of knots, and determining if alignment errors are present.

13. The method of claim 10, wherein the step of extracting physical features comprises:
identifying a plurality of segments of the suture;
measuring offset lengths of simulated tissue;
converting the offset lengths into physical coordinates; and
extracting image coordinates of suture knots of the suture, entry and exits points, and suture line of the suture, wherein the image coordinates are used to score the suture.

14. The method of claim 10, wherein the quality of the suture is based on spacing of the suture, symmetry of the suture, degree of eversion/inversion, pitch, and offset of tissue.

15. The method of claim 10, wherein the step of scoring the suture comprises displaying an image of the suture to a user for manual grading.

16. The method of claim 10, wherein the suture training apparatus is configurable with a plurality of orientations of the simulated tissue, wherein the plurality of orientations are objective based on one or more of the plurality fiducial markings on the suture training apparatus.

17. The method of claim 16, wherein the rating and complexity of the suture are based in part on an orientation of the simulated tissue when the suture was performed.

18. The method of claim 10, wherein the one or more servers reside in a cloud.

19. A suture training system, comprising:
a suture training apparatus configurable with a plurality of orientations of simulated tissue to simulate natural anatomical orientations encountered in actual surgery, wherein the plurality of simulated tissue orientations are objective based on one or more of a plurality of fiducial markings on the suture training apparatus;
an image analysis system configured to receive a video of a suture performed using the suture training apparatus and the simulated tissue;
a feature extraction system configured to extract physical features of the suture from the video;
a suture grading system configured to score the suture based on the extracted physical features of the suture and based on a rating and complexity of the suture to determine a quality of the suture in an objective manner, the rating and complexity of the suture based in part on the orientation of the simulated tissue when the suture was performed; and
a recommendation engine configured to recommend training based on the score and the extracted features,
wherein each of the image analysis system, the feature extraction system, the suture grading system, and the recommendation engine are executed on one or more servers, and
wherein the plurality of fiducial markings include fiducial markings on a base of the suture training apparatus providing an angle of a holder of the suture training apparatus relative to the base and fiducial markings on joints of the suture training apparatus providing (1) yaw or pitch of an arm of the suture training apparatus and (2) pitch or roll of the holder.

20. The suture training system of claim 19, wherein the feature extraction system, the suture grading system, and the recommendation engine are implemented in a cloud.

* * * * *